United States Patent [19]

Krapcho et al.

[11] 4,053,514
[45] Oct. 11, 1977

[54] 2-[DIALKYLAMINOALKOXYPHENYL]-METHYLENE-2,3-DIHYDRO-1H-INDEN-1-ONES AND THE SALTS THEREOF

[75] Inventors: John Krapcho; Joseph Schwartz, both of Somerset, N.J.

[73] Assignee: E. R. Squibb & Sons, Inc., Princeton, N.J.

[21] Appl. No.: 682,695

[22] Filed: May 3, 1976

Related U.S. Application Data

[62] Division of Ser. No. 599,732, July 28, 1975, Pat. No. 3,969,527.

[51] Int. Cl.$^2$ ............................................. C07C 93/06
[52] U.S. Cl. ................................. 260/570 R; 260/253; 260/501.11; 260/501.18; 260/501.19; 260/570.7; 542/428; 542/429
[58] Field of Search ..................... 260/501.18, 501.19, 260/570.7, 570 R

[56] References Cited

U.S. PATENT DOCUMENTS

| 3,160,656 | 12/1964 | Krapcho | 260/570.7 X |
| 3,350,405 | 10/1967 | Schulenberg et al. | 260/570.7 X |
| 3,506,653 | 4/1970 | Fried | 260/570.7 X |
| 3,592,819 | 7/1971 | Fleming et al. | 260/570.7 X |
| 3,716,531 | 2/1973 | Albrecht et al. | 260/570.7 X |

Primary Examiner—Robert V. Hines
Attorney, Agent, or Firm—Lawrence S. Levinson; Merle J. Smith; Burton Rodney

[57] ABSTRACT

Compounds of the formula

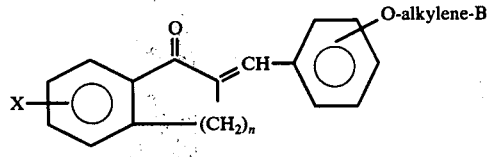

wherein X, $n$ and B are as defined herein are useful as intermediates in preparing compounds which exhibit antidepressant activity.

11 Claims, No Drawings

2-[DIALKYLAMINOALKOXYPHENYL]-METHYLENE-2,3-DIHYDRO-1H-INDEN-1-ONES AND THE SALTS THEREOF

REFERENCE TO OTHER APPLICATIONS

This application is a divisional application of Ser. No. 599,732, filed July 28, 1975 and now U.S. Pat. No. 3,969,527.

SUMMARY OF THE INVENTION

Compounds of the formula

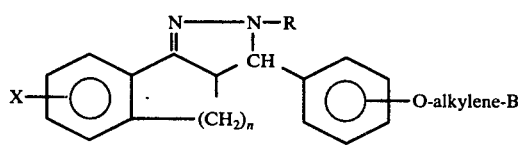

wherein $n$ is 1, 2 or 3, R is H, lower alkyl, lower alkanoyl, aryl, hydroxy lower alkyl and aralkyl; X is H, halogen, preferably Cl or F, lower alkyl, lower alkoxy or $CF_3$; and B is lower alkylamino, dilower alkylamino, piperidino, pyrrolidono, morpholino, N-lower alkylpiperazino, or N-(2-hydroxyethyl)piperazino; and the N-oxides and pharmaceutically acceptable acid-addition salts thereof have been found to exhibit antidepressant activity in mammalian species, e.g., mice, rats, dogs, cats and the like, and are used in the same manner as imipramine.

The term "lower alkyl" is intended to mean a straight or branched hydrocarbon fragment of from 1 to 8 carbons, preferably from 1 to 4 carbons.

The term "lower alkoxy" is intended to mean "lower alkyl—O—".

The term "lower alkanoyl" is intended to mean "lower

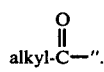

The term "alkylene" as employed herein refers to a straight or branched saturated hydrocarbon chain having from 2 to 5 carbon atoms, such as ethylene, propylene, butylene and pentylene.

The term "aryl" as employed herein refers to aromatic radicals such as phenyl and pyridyl.

The term "aralkyl" as employed herein refers to a lower alkyl group of from 1 to 8 carbons having an aryl substituent, such as benzyl and phenethyl.

Preferred are those compounds wherein R is H or lower alkyl, X is H, $n$ is 1 or 2, B-alkylene—O— is in the para position, alkylene is —$(CH_2)_3$—, and B is dilower alkylamino.

DETAILED DESCRIPTION

The compounds of the present invention may be prepared by reacting a ketone of formula II wherein X and $n$ are as defined above

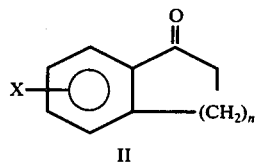

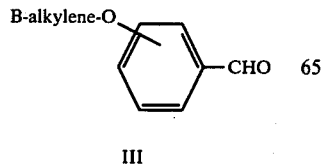

with a B-alkylene-O-benzaldehyde compound of formula III in a polar solvent, preferably an aliphatic alkanol of from 1 to 5 carbons or dimethylformamide, at lowered temperatures of from 0° C to about −25° C, preferably in the presence of a base such as an alkali metal hydroxide, for example, potassium hydroxide or sodium hydroxide, to form a ketone of the formula IV

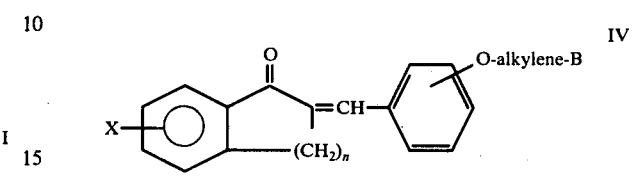

The formula IV compound is reacted with an R-substituted hydrazine compound of the formula V to produce the final product of formula I.

$H_2NNHR$

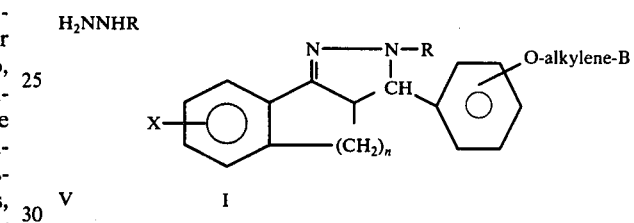

V          I

The latter reaction takes place by refluxing in a polar organic solvent, preferably an aliphatic alkanol of from 1 to 5 carbons or dimethylformamide, at a temperature of from about 40° C to about 120° C, preferably at about the reflux temperature of the solvent, for from about ½ hour to about 12 hours, preferably for from about 2 to about 6 hours.

Where R is hydrogen in the compound of formula I, the hydrogen may be converted to a lower alkanoyl group by heating the former (R=H) with the appropriate lower alkanoyl halide or anhydride, for example, acetyl chloride or acetic anhydride.

The starting compounds of formula II may be prepared by reacting a phenylalkanoic acid of the formula VI

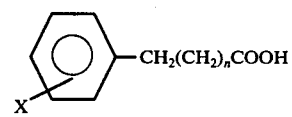

with polyphosphoric acid by known methods, or with $SOCl_2$ followed by $AlCl_3$ by known methods, to produce a ketone of the formula

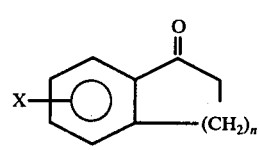

The aldehyde starting materials of formula III may be prepared by treating a hydroxy aldehyde of the structure

VII

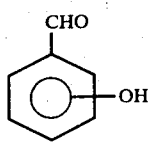

with alkaline reagents such as sodium hydride to give the appropriate sodium salt and then treating the sodium salt with a halo compound of the structure Hal-alkylene B.                                            (VIII)

The compounds of the present invention, their N-oxides and their pharmaceutically acceptable acid-addition salts are antidepressants in mammals, e.g., dogs, cats, mice and rats, and are effective as antidepressants (particularly in relieving endogenous depression) as evidenced by their ability to reverse tetrabenazine induced ptosis in mice ["Psychosomatic Medicine", Nodine and Moyer, 1962, pages 683–690[. The compound of the invention may be administered in amounts ranging from about 0.5 mg to about 10.0 mg per kg of body weight per day to produce the above effects. A preferred dosage regimen for optimum results would be from about 1 mg to about 5 mg per kg of body weight per day, and such dosage units are employed that a total of from about 35 mg to about 7 g of active ingredient for a subject of about 70 kg body weight are administered in a 24 hour period.

As to the pharmaceutically acceptable salts, those coming within the purview of the invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic acid, theophylline, 8-chlorotheophylline, p-aminobenzoic, p-acetamidobenzoic, or methanesulfonic.

The N-oxide derivatives of the compounds of the present invention are prepared by treating the free base with excess aqueous $H_2O_2$ in known manner. The N-oxide may, if desired, be converted to one of the above pharmaceutically acceptable acid-addition salts in the usual manner.

The compounds of the present invention in the described dosages are intended to be administered orally; however, other routes, such as rectally, intaperitoneally, subcutaneously, intramuscularly or intravenously may be employed.

The active compounds of the present invention are orally administered, for example, with an inert diluent or with an assimilable edible carrier, or they may be enclosed in hard of soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between 2 and 500 milligrams of active compound, preferably between 2 and 25 mg.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples illustrate the present invention without, however, limiting the same thereto. All temperatures are expressed in degrees Centigrade.

EXAMPLE 1

3-[4-[2-(Diethylamino)ethoxy]phenyl]-2,3,3a,4-tetrahydro-2-methyl-indeno[1,2-c]pyrazole, hydrochloride (1:2)

A.

2-[[4-[(Diethylamino)ethoxy]phenyl]methylene]-2,3-dihydro-1H-inden-1-one, hydrochloride salt (1:1)

A mixture of 50 g (0.38 mole) of 1-indanone, 84 g (0.38 mole) of 4-diethylaminoethoxy benzaldehyde and 250 ml of ethanol is cooled to −10° and treated with a solution of 2.5 g of KOH in 50 ml of ethanol. After the exothermic reaction subsides, the mixture is stirred at room temperature for 1 hour (product begins to crystallize) and is poured onto 1 liter of ice-water. The resulting solid is filtered, washed with cold water and dried to give 119 g of yellow material, mp 90°–92°. Recrystallization from 400 ml of MeCN yields 109.1 g (86%) of yellow crystals mp 94°–96°.

A solution of 3 g of the above in 25 ml of warm MeCN is treated with 1 equivalent of ethanolic HCl. On cooling, 3.2 g of yellow crystals are collected, mp 206°–209°. Crystallization from 20 ml of ethanol gives 2.8 g (84%) of the title Compound A in the form of yellow crystals, mp 208°–210°.

B.

3-[4-[2-(Diethylamino)ethoxy]phenyl]-2,3,3a,4-tetrahydro-2-methyl-indeno[1,2-c]pyrazole A solution of 26.4 g (0.08 mole) of 2-[[4-2-(diethylamino) ethoxy]phenyl]methylene]-2,3-dihydro-1H-inden-1-one in 250 ml of methanol containing 3.7 g (0.08 mole) of methyl hydrazine is heated at reflux for 4 hours. After cooling, 9.1 g starting material is recovered.

The filtrate is concentrated to an oil, dissolved in ether and cooled overnight to crystallize 3.9 g of starting material. The ether is evaporated to a clear viscous oil (15.9 g).

The above is chromatographed over 300 g of Woelm Alumina IV. Using 800 ml of 50% hexene-benzene, a total of 5.1 g of an unknown material is collected. Continued elution with the same solvent (600 ml) gives 2.7 g of material which crystallizes from an oil residue after the solvent is evaporated, mp 73°–76°.

The above is combined with 1.4 g of comparable material (ir, mp) prepared in an earlier experiment. A solution of this material (4.1 g) in 30 ml of refluxig hexane is cooled to give 3.2 g of the title B compound in the form of cream-colored crystals, mp 75°–77°.

C.
3-[4-[2-(Diethylamino)ethoxy]phenyl]-2,3,3a,4-tetrahydro-2-methyl-indeno[1,2-c]pyrazole, hydrochloride (1:2)

A solution of the compound prepared as described in part B in 25 ml of warm MeCn is treated with 2 equivalents of ethanolic HCl to crystallize 4.0 g of nearly colorless crystals, mp 213°–216° dec., s. 180°. Crystallization from 20 ml of methanol yields 2.9 g (10%) (based on consumed starting material) of colorless crystals, mp 215°–217° dec., s. 198°.

EXAMPLE 2

3-[4-[3-(Dimethylamino)propoxy]phenyl]-2,3,3a,4-tetrahydro-2-methylindeno[1,2-c]pyrazole, hydrochloride (1:1)

A. 4-(3-Dimethylaminopropoxy)benzaldehyde

A stirred solution of 61.0 g (0.50 mole) of 4-hydroxybenzaldehyde in 400 ml of dimethylformamide (nitrogen atmosphere) is gradually treated with 24.0 g of 50% NaH. The temperature is kept below 35° using an ice water bath. When the addition is completed, the thick mixture is heated to 70° for several minutes, then cooled to 35° before the addition of 417 ml of 1.8N (0.75 mole) of 3-dimethylaminopropyl chloride in toluene.

The mixture is stirred and heated at 100°–105° for 3 hours. The sodium salt of the hydroxybenzaldehyde, which has limited solubility in dimethylformamide, appears to react with the halide when the temperature approaches 90°. The color changes from lavender to brown.

After cooling, the mixture is poured over 1 liter of ice-water, then extracted with 300 ml of ether (2×). The ether phases are combined, washed with water, then treated with 125 ml of 6N HCl. After separation of the aqueous layer, the ether fraction is washed with water.

The aqueous portions are combined and treated with an excess of K₂CO₃ to liberate the base into ether. The solvent is dried (MgSO₄), evaporated, and the residue is distilled to give 68.8 g (67%) of colorless product, bp 145°–148°/1.5 mm.

B.
2-[[4-[3-(Dimethylamino)propoxy)]phenyl]-methylene]-2,3-dihydro-1H-inden-1-one, hydrochloride (1:1)

The reaction between 26.4 g (0.20 mole) of 1-indanone and 41.5 g (0.20 mole) of the above in a procedure described for Example 1, part A, gives 48.7 g of greenish yellow material, mp 82°–85°, s 78°. Crystallization from 100 ml of MeCN yields 43.5 g (68%) of yellow crystals, mp 84°–86°.

A solution of 3.0 g of the above in 25 ml of warm MeCN is treated with one equivalent of ethanolic HCl to give 3.0 g of light yellow crystals, mp 239°–241°. A solution of this material in 60 ml of methanol is concentrated to approximately one-half volume and cooled to yield 2.6 g (78%) of cream colored crystals, mp 239°–241°.

C.
3-[4-[3-(Dimethylamino)propoxy]phenyl]-2,3,3a,4-tetrahydro-2-methylindeno[1,2-c]pyrazole, hydrochloride (1:1)

A mixture of 12.0 g (0.033 mole) of 2-[[4-[3-(dimethylamino)propoxy]phenyl]methylene]-2,3-dihydro-1H-inden-1-one, hydrochloride from part B and 1.7 g (0.037 mole) of methyl hydrazine in 60 ml of methanol is stirred and heated. The resulting solution is refluxed for 4 hours. After cooling, the solvent is evaporated to give 13.3 g of a viscous oil. This material is dissolved in 30 ml of acetone and cooled to yield 9.4 g of a yellow solid, mp 165°–170°, s. 140°.

A solution of the above product in 25 ml of H₂O is filtered to remove a small quantity of insoluble material and then treated with an excess of K₂CO₃. The base is extracted into ether, dried (MgSO₄) and concentrated to give 6.8 g of an oily residue.

A solution of the above base in 25 ml of acetone is treated with one equivalent of ethanolic HCl to give 5.0 g of a light tan solid, mp 185°–187°. Crystallization from 10 ml of ethanol yields 3.2 g (25%) of cream-colored crystals, mp 188°–190°.

EXAMPLE 3

3-[4-[2-(Dimethylamino)ethoxy]phenyl]-2,3,3a,4-tetrahydro-2-methyl-indeno[1,2-c]pyrazole, hydrochloride (1:1)

A. 4-(2-Dimethylaminoethoxy)benzaldehyde

The reaction between 61.0 g (0.50 mole) of 4-hydroxybenzaldehyde, 24.0 g of 50% NaH, and 341 ml of 2.2 N (0.75 mole) 2-dimethylaminoethyl chloride in toluene in a procedure described for Example 2, part A gives 45.0 g (46%) of colorless product, bp 140°–142°/2 mm. Lit. bp 185°–187°/15 mm.

B.
2-[[4-[2-(Dimethylamino)ethoxy]phenyl]methylene]-2,3-dihydro-1H-inden-1-one, hydrochloride (1:1)

The reaction between 31 g (0.23 mole) of 1-indanone and 45 g (0.23 mole) of material from part A according to a procedure described for Example 1, part A, gives 58.5 g of yellow crystals, mp 95°–97°, s. 92°. Crystallization from 130 ml of MeCN yields 53.2 g (75%) of cream-colored crystals, mp 107°–109°.

A solution of 6.0 g of the above in 50 ml of warm MeCN is treated with one equivalent of ethanolic HCl to give 6.4 g of light yellow solid, mp 237°–239°. Crystallization from 30 ml of methanol yields 5.49 g of nearly colorless crystals, mp 234°–238° (solvated with methanol).

The above is recrystallized from a solution containing 22.5 ml of MeCN and 2.5 ml of H₂O ml to give 4.8 g (68%) of a cream-colored hydrated product, mp 237°–239°, s. 233°.

C. 3-[4-[2-(Dimethylamino)ethoxy]phenyl]-2,3,3a,4-tetrahydro-2-methyl-indeno[1,2-d]pyrazole, hydrochloride (1:1)

A mixture of 10.0 g (0.029 mole) of 2-[[4-[2-(dimethylamino)ethoxy]-phenyl]-methylene]-2,3-dihydro-1H-inden-1-one,hydrochloride, part B, and 1.4 g (0.031 mole) of methyl hydrazine in 50 ml of methanol is stirred at reflux temperature for 4 hours. After cooling, the solvent is evaporated and the residue (oil) is dissolved in 25 ml of acetone to crystallize 9.1 g of the crude hydrochloride salt, mp 165°–168°, s. 150°.

A solution of the above (9.0 g) in 25 ml of water is treated with an excess of $K_2CO_3$. The base is extracted with ether, dried ($MgSO_4$), and evaporated to give an oily residue. This material (6.9 g) crystallizes on standing at room temperature to a light tan solid, mp 70°–72°.

The above material is combined with 2.7 g of comparable product prepared in a previous experiment, and recrystallized from 30 ml of cyclohexane to give 7.6 g (55%) of yellow crystals, mp 70°–72°.

A solution of the above (7.6 g) in 50 ml of warm acetone is treated with 1 equivalent of ethanolic HCl to crystallize 5.2 g of a cream-colored solid, mp 185°–187°. Crystallization of this material from 40 ml of MeCN and 0.25 ml of $H_2O$ gives 3.9 g of nearly colorless solid, mp 190°–192°.

The above is treated with 75 ml of hot isopropyl alcohol. A small amount of insoluble material is removed by filtration and the filtrate is cooled to give 3.3 g (40%) of nearly colorles product, mp 190°–192°.

EXAMPLE 4

3-[3-[3-(Dimethylamino)propoxy]phenyl]-2,3,3a,4-tetrahydro-2-methylindeno[1,2-c]pyrazole, hydrochloride (1:1)

A. 3-(3-Dimethylaminopropoxy)benzaldehyde

The reaction between 61.0 g (0.50 mole) of 3-hydroxybenzaldehyde, 24.0 g of 50% NaH (0.50 mole), and 396 ml of 1.89N (0.75 mole) of 3-dimethylaminopropyl chloride in toluene in a procedure described for Example 2, part A, gives 69.0 g (66%) of colorless product, bp 155°–158°/3 mm.

B. 2-[[3-[3-(Dimethylamino)propoxy]phenyl]methylene]-2,3-dihydro-1H-inden-1-one, hydrochloride (1:1)

A stirred solution of 44.0 g (0.33 mole) of 1-indanone and 69.0 g (0.33 mole) of the material from part A in 250 ml of ethanol is cooled to −10° and treated gradually with a solution of 2.0 g of KOH in 25 ml of ethanol according to a procedure described in Example 1, part A.

The oil product is extracted with 200 ml of ether (2×). The solvent portions are combined, washed with water, dried ($MgSO_4$) and evaporated to give 103.8 g of a yellow oily product.

A solution of 25 g of the above base in 60 ml of MeCN is treated with one equivalent of HCl in ethanol to give 16.7 g of nearly colorless solid, mp 197°–199°. Recrystallization from a solution of 60 ml of ethanol and 30 ml of methanol yields 13.6 g (48%) of colorless product, mp 198°–200°.

C. 3-[3-[3-(Dimethylamino)propoxy]phenyl]-2,3,3a,4-tetrahydro-2-methylindeno[1,2-c]pyrazole, hydrochloride (1:1)

A stirred solution of 8.6 g (0.024 mole) of 2-[[3-[3-(dimethylamino)propoxy]phenyl]methylene]-2,3-dihydro-1H-inden-1-one hydrochloride from part B and 1.3 g (0.028 mole) of methyl hydrazine in 50 ml of methanol is heated at reflux for 2 hours. After cooling, the solvent is evaporated to give 1.0 g of an amber oily residue.

A solution of this material in 50 ml of acetone is cooled overnight to yield 4.3 g of tan solid, mp 165°–170°. Crystallization from 20 ml of MeCN gives 2.3 g (25%) of cream colored solid, mp 177°–179°. A sample of this material is recrystallized from MeCN, mp at 177°–179°.

EXAMPLE 5

3-[2-[3-(Dimethylamino)propoxy]phenyl]-2,3,3a,4-tetrahydro-2-methylindeno[1,2-c]pyrazole, oxalate salt

A. 2-(3-Dimethylaminopropoxy)benzaldehyde

The reaction between 100 g (0.82 mole) of salicylaldehyde, 40 g (0.82 mole) of 50% NaH, and 650 ml (1.2 mole) of 1.89 N 3-dimethylaminopropyl chloride in toluene in a procedure described in Example 2, part A, gives 130.4 g (77%) of yellow product, bp 125°–130°/0.5 mm.

2-[[2-[3-(Dimethylamino)propoxy]phenyl]methylene]-2,3-dihydro-1H-inden-1-one, hydrochloride (1:1)

The reaction between 88 g (0.42 mole) of the benzaldehyde from Part A and 56 g (0.42 mole) of 1-indanone in a procedure described in Example 1, part A, gives 134.2 g of a yellow oily product.

A solution of 26 g of the above product in 50 ml of acetone is treated with one equivalent of HCl in ethanol to give 24.6 g of light yellow crystals, mp 178°–182°. Crystallization from 100 ml of ethanol yields 18.9 g (64%) of cream colored crystals, mp 184°–186°.

C. 3-[2-[3-(Dimethylamino)propoxy]phenyl]-2,3,3a,4-tetrahydro-2-methylindeno[1,2-c]pyrazole, oxalate salt A solution of 10.0 g (0.028 mole) of 2-[[2-[3-dimethylamino)propoxy]phenyl]methylene]-2,3-dihydro-1H-inden-1-one, hydrochloride from part B in 60 ml of methanol is reacted with 1.5 g (.032 mole) of methyl hydrazine in a procedure described in Example 1, part B, to give 9.0 g of an oily product.

A solution of 8.0 g of the above material in 25 ml of acetone is treated with a solution of one equivalent (2.1 g) of oxalic acid in 25 ml of acetone. The resulting solution is gradually diluted with 50 ml of ether to form 8.2 g of yellow solid, mp 129°–131°, s. 80°. Following recrystallization from acetone-methanol and then from ethanol, the product melts at 151°–153°.

EXAMPLE 6

3-[4-[2-(Dimethylamino)ethoxy]phenyl]-3,3a,4,5-tetrahydro-2-methyl-2H-naphtho[1,2-c]pyrazole, hydrochloride (1:2)

A.
2-[[4-[2-(Diethylamino)ethoxy]phenyl]methylene]-3,4-dihydro-1( 2H)-naphthalenone, hydrochloride (1:1)

A stirred solution of 13.2 g (0.09 mole) of α-tetralone and 20 g (0.09 mole) of 4-(diethylaminoethoxy)benzaldehyde in 75 ml of ethanol is cooled to −20° and treated with a solution of 0.6 g of KOH in 20 ml of ethanol. The icebath is removed and the mixture is allowed to warm to 25°. After standing overnight, the solution is filtered to remove a small amount of unknown material.

After evaporation of the solvent, the oil residue is dissolved in ether and extracted with water (3×), dried (MgSO$_4$) and concentrated to give 34 g of an oil. This material solidifies and is treated with hexane, then cooled overnight to give 20 g of tan crystals, mp 50°-52°. A solution of this material in 20 ml of warm isopropyl ether is diluted with 20 ml of hexane to slowly crystallize 15.3 g (50%) of cream-colored material, mp 50°-52°.

A solution of 3.0 g of the above in 15 ml of MeCN is treated with 1 equivalent of ethanolic HCl to give 2.8 g of orange solid, mp 154°-156°. Crystallization from 5 ml of ethanol yields 2.1 g (64%) of yellow crystals, mp 168°-170°.

B. 3-[4-[2-(Diethylamino)ethoxy]phenyl]-3,3a,4,5-tetrahydro-2-methyl-2H-naphtho[1,2-c]pyrazole, hydrochloride (1:2)

A solution of 10.0 g (0.028 mole) of the base from part A and 6.5 g (0.14 mol) of methyl hydrazine in 75 ml of methanol is refluxed for 4 hours. After cooling, the solvent is evaporated to give a solid residue. Trituration with hexane gives 9.4 g of nearly colorless solid, mp 62°-64°. The ir spectrum of this material is in accord with the expected structure. Crystallization from 40 ml of isopropyl ether yields 7.1 g of nearly colorless crystals, mp 73°-75°.

A solution of the above in 20 ml of ethanol containing 2 equivalents of ethanolic HCl is diluted with 50 ml of of MeCn and concentrated to approximately one-half volume. This solution is seeded and cooled to give 7.6 g of colorless crystals, mp 211°-213° (dec). Crystallization from 20 ml of ethanol yields 6.0 g (48%) of product, mp 211°-213° (dec).

EXAMPLES 7 – 23

Following the procedure of Example 1 but substituting for the benzaldehyde in part A an equivalent amount of the substituted benzaldehyde of column I, there is obtained, respectively, the corresponding compound of the formula

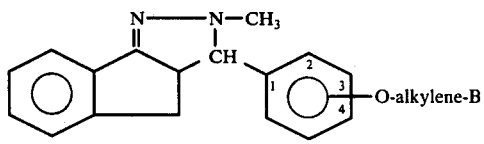

wherein B-alkylene is as indicated in column II:

| Example | I | II B-alkylene | (Position of substitution) |
|---|---|---|---|
| 7 | 4-[4-(dimethylamino)butoxy]benzaldehye | (CH$_3$)$_2$N(CH$_2$)$_4$ | (4) |
| 8 | 4-[3-(n-propylamino)propoxy]benzaldehyde | (n-C$_3$H$_7$)HN(CH$_2$)$_3$ | (4) |
| 9 | 4-[2-(ethylmethylamino)ethoxy]benzaldehyde | (CH$_3$)(C$_2$H$_5$)N(CH$_2$)$_2$ | (4) |
| 10 | ⟨N—(CH$_2$)$_5$—O—⟨⟩—CHO | ⟨N—(CH$_2$)$_5$ | (4) |
| 11 | ⟨N—(CH$_2$)$_3$—O—⟨⟩—CHO | ⟨N—(CH$_2$)$_3$ | (4) |
| 12 | CH$_3$—N⟨⟩N—(CH$_2$)$_2$—O—⟨⟩—CHO | CH$_3$—N⟨⟩N—(CH$_2$)$_2$ | (4) |
| 13 | O⟨⟩N—(CH$_2$)$_3$—O—⟨⟩—CHO | O⟨⟩N—(CH$_2$)$_3$ | (4) |
| 14 | HOCH$_2$CH$_2$N⟨⟩N—(CH$_2$)$_3$—O—⟨⟩—CHO | HOCH$_2$CH$_2$N⟨⟩N—(CH$_2$)$_3$ | (4) |
| 15 | 3-[2-(diethylamino)ethoxy]benzaldehyde | (C$_2$H$_5$)$_2$N(CH$_2$)$_2$ | (3) |
| 16 | 3-[2-(ethylamino)ethoxy]benzaldehyde | (C$_2$H$_5$)HN(CH$_2$)$_2$ | (3) |
| 17 | 2-[3-(n-propylamino)propoxy]benzaldehyde | (n-C$_3$H$_7$)HN(CH$_2$)$_3$ | (2) |
| 18 | 2-[2-(diethylamino)ethoxy]benzaldehyde | (C$_2$H$_5$)$_2$N(CH$_2$)$_2$ | (2) |
| 19 | ⟨N—(CH$_2$)$_2$O—⟨⟩—CHO | ⟨N—(CH$_2$)$_2$ | (3) |
| 20 | ⟨N—(CH$_2$)$_3$—O—⟨⟩—CHO (CHO at 2) | ⟨N—(CH$_2$)$_3$ | (2) |
| 21 | CH$_3$—N⟨⟩N—(CH$_2$)$_3$—O—⟨⟩—CHO | CH$_3$—N⟨⟩N—(CH$_2$)$_2$ | (3) |

-continued

| Example | I | II B-alkylene | (Position of substitution) |
|---|---|---|---|
| 22 | morpholine-N-(CH₂)₃-O-[2-CHO-phenyl] | morpholine-N-(CH₂)₃ | (2) |
| 23 | HOCH₂CH₂N-piperazine-N-(CH₂)₃-O-[phenyl]-CHO | HOCH₂CH₂N-piperazine-N-(CH₂)₃ | (3) |

EXAMPLES 24 – 41

Following the procedure of Example 6 but substituting for benzaldehyde in part A an equivalent amount of the substituted benzaldehyde of column I, there is obtained, respectively, the corresponding compound of the formula

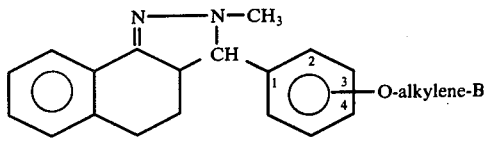

wherein B-alkylene is as indicated in column II:

| Example | I B-alkylene | II (position) | |
|---|---|---|---|
| 24 | 4-[2-(diethylamino)ethoxy]benzaldehyde | $(C_2H_5)_2N(CH_2)_2$ | (4) |
| 25 | 4-[3-(dimethylamino)propoxy]benzaldehyde | $(CH_3)_2N(CH_2)_3$ | (4) |
| 26 | 4-[4-(n-propylamino)butoxy]benzaldehyde | $(n\text{-}C_3H_7)HN(CH_2)_4$ | (4) |
| 27 | 4-[2-(ethylmethylamino)ethoxy]benzaldehyde | $(CH_3)(C_2H_5)N(CH_2)_2$ | (4) |
| 28 | hexamethyleneimine-N-(CH₂)₃-O-[4-CHO-phenyl] | hexamethyleneimine-N-(CH₂)₃ | (4) |
| 29 | aziridine-N-(CH₂)₂-O-[4-CHO-phenyl] | aziridine-N-(CH₂)₂ | (4) |
| 30 | C₂H₅-piperazine-N-(CH₂)₃-O-[4-CHO-phenyl] | C₂H₅-piperazine-N-(CH₂)₃ | (4) |
| 31 | morpholine-N-(CH₂)₂-O-[4-CHO-phenyl] | morpholine-N-(CH₂)₂ | (4) |
| 32 | HOCH₂CH₂N-piperazine-N-(CH₂)₂-[4-CHO-phenyl] | HOCH₂CH₂N-piperazine-N-(CH₂)₂ | (4) |
| 33 | 3-[2-(diethylamino)ethoxy]benzaldehyde | $(C_2H_5)_2N(CH_2)_2$ | (3) |
| 34 | 3-[3-(dimethylamino)propoxy]benzaldehyde | $(CH_3)_2N(CH_2)_3$ | (3) |
| 35 | 2-[4-dimethylamino)butoxy]benzaldehyde | $(CH_3)_2N(CH_2)_4$ | (2) |
| 36 | 2-[2-ethylmethylamino)ethoxy]benzaldehyde | $(CH_3)(C_2H_5)N(CH_2)_2$ | (2) |
| 37 | hexamethyleneimine-N-(CH₂)₃-O-[3-CHO-phenyl] | hexamethyleneimine-N-(CH₂)₃ | (3) |
| 38 | aziridine-N-(CH₂)₅-O-[2-CHO-phenyl] | aziridine-N-(CH₂)₅ | (2) |
| 39 | C₂H₅-piperazine-N-(CH₂)₃-O-[3-CHO-phenyl] | C₂H₅-piperazine-N-(CH₂)₃ | (3) |

-continued

| Example | I B-alkylene | II | (position) |
|---|---|---|---|
| 40 | ![morpholine-N-(CH3)2-O-benzaldehyde] O\N—(CH3)2—O—C6H4—CHO | O\N—(CH2)2 | (2) |
| 41 | HOCH2CH2N\N—(CH2)2—C6H4—CHO | HOCH2CH2N\N—(CH2)2 | (3) |

EXAMPLES 42 – 59

Following the procedure of Example I but substituting for benzaldehyde in part A an equivalent amount of the substituted benzaldehyde of column I, and substituting for indanone an equivalent amount of suberone, there is obtained, respectively, the corresponding compound of the formula

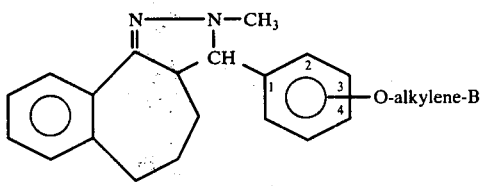

wherein B-alkylene is as indicated in column II

| Example | I | II | (position) |
|---|---|---|---|
| 42 | 4-[2-diethylamino)ethoxy]benzaldehyde | $(C_2H_5)_2N(CH_2)_2$ | (4) |
| 43 | 4-[3-(dimethylamino)propoxy]benzaldehyde | $(CH_3)_2N(CH_2)_3$ | (4) |
| 44 | 4-[4-(n-propylamino)butoxy]benzaldehyde | $(n-C_3H_7)HN(CH_2)_4$ | (4) |
| 45 | 4-[2-(ethylmethylamino)ethoxy]benzaldehyde | $(CH_3)(C_2H_5)N(CH_2)_2$ | (4) |
| 46 | ⟨N—(CH2)3—O—C6H4—CHO⟩ (pyrrolidine) | ⟨N—(CH2)3⟩ | (4) |
| 47 | ⟨N—(CH2)2—O—C6H4—CHO⟩ (aziridine) | ⟨N—(CH2)2⟩ | (4) |
| 48 | C2H5—N\N—(CH2)5—O—C6H4—CHO | C2H5—N\N—(CH2)5 | (4) |
| 49 | O\N—(CH2)2—O—C6H4—CHO | O\N—(CH2)2 | (4) |
| 50 | HOCH2CH2N\N—(CH2)2—C6H4—CHO | HOCH2CH2N\N—(CH2)2 | (4) |
| 51 | 3-[2-(diethylamino)ethoxy]benzaldehyde | $(C_2H_5)_2N(CH_2)_2$ | (3) |
| 52 | 2-[3-(dimethylamino)propoxy]benzaldehyde | $(CH_3)_2N(CH_2)_3$ | (2) |
| 53 | 3-[4-(n-propylamino)butoxy]benzaldehyde | $(n-C_3H_7)HN(CH_2)_4$ | (3) |
| 54 | 2-[2-ethylmethylamino)ethoxy]benzaldehyde | $(CH_3)(C_2H_5)N(CH_2)_2$ | (2) |
| 55 | ⟨N—(CH2)3—O—C6H4—CHO⟩ | ⟨N—(CH2)3⟩ | (3) |
| 56 | ⟨N—(CH2)2—O—C6H4—CHO⟩ | ⟨N—(CH2)2⟩ | (2) |
| 57 | C2H5—N\N—(CH2)3—O—C6H4—CHO | C2H5—N\N—(CH2)3 | (3) |
| 58 | O\N—(CH3)2—O—C6H4—CHO | O\N—(CH2)2 | (2) |
| 59 | HOCH2CH2N\N—(CH2)2—C6H4—CHO | HOCH2CH2N\N—(CH2)2 | (2) |

EXAMPLES 60 – 83

Following the procedure of Example 1 but substituting for the benzaldehyde in part A an equivalent amount of the substituted benzaldehyde of column I and sustituting for methylhydrazine in part B an equivalent amount of the compound listed in column II, there is obtained, respectively, the corresponding compound of the formula

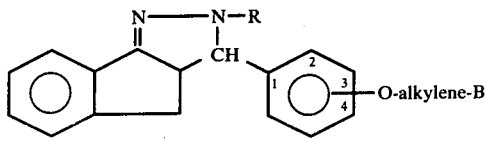

wherein B-alkylene is the radical indicated in column III and R is the radical indicated in column IV.

| Ex. | I | II | III B-alkylene | (position) | IV R |
|---|---|---|---|---|---|
| 60 | OHC—⟨phenyl⟩—O—(CH$_2$)$_2$—N—(CH$_3$)$_2$ | H$_2$NNHC$_2$H$_5$ | (CH$_3$)$_2$N(CH$_2$)$_2$ | (4) | C$_2$H$_5$ |
| 61 | OHC—⟨phenyl⟩—O—(CH$_2$)$_4$—NH(n-C$_3$H$_7$) | H$_2$NNHn-C$_3$H$_7$ | (n-C$_3$H$_7$)HN(CH$_2$)$_4$ | (4) | n-C$_3$H$_7$ |
| 62 | OHC—⟨phenyl⟩—O—(CH$_2$)$_3$—N⟨piperidine⟩ | H$_2$NNHCH$_2$C$_6$H$_5$ | ⟨piperidine⟩N—(CH$_2$)$_3$ | (4) | CH$_2$C$_6$H$_5$ |
| 63 | OHC—⟨phenyl⟩—O—(CH$_2$)$_3$—N⟨pyrrolidine⟩ | H$_2$NNHCH$_2$CH$_2$C$_6$H$_5$ | ⟨pyrrolidine⟩N—(CH$_2$)$_3$ | (4) | CH$_2$CH$_2$C$_6$H$_5$ |
| 64 | OHC—⟨phenyl⟩—O—(CH$_2$)$_3$—N⟨morpholine⟩O | H$_2$NNH$_2$ | O⟨morpholine⟩N—(CH$_2$)$_3$ | (4) | H |
| 65 | OHC—⟨phenyl⟩—O—(CH$_2$)$_3$—N⟨piperazine⟩N—CH$_3$ | H$_2$NNHn-C$_3$H$_7$ | CH$_3$—N⟨piperazine⟩N—(CH$_2$)$_3$ | (4) | n-C$_3$H$_7$ |
| 66 | OHC—⟨phenyl⟩—O—(CH$_2$)$_3$—N⟨piperazine⟩N—CH$_2$CH$_2$OH | H$_2$NNHCH$_2$C$_6$H$_5$ | HOCH$_2$CH$_2$—N⟨piperazine⟩N—(CH$_2$)$_3$ | (4) | CH$_2$C$_6$H$_5$ |
| 67 | OHC—⟨phenyl⟩—O—(CH$_2$)$_2$—N(C$_2$H$_5$)$_2$ | H$_2$NNHC$_6$H$_5$ | (C$_2$H$_5$)$_2$N—(CH$_2$)$_2$ | (4) | C$_6$H$_5$ |
| 68 | OHC—⟨phenyl⟩—O—(CH$_2$)$_5$—NHCH$_3$ | H$_2$NNHCCH$_3$ ‖ O | CH$_3$NH(CH$_2$)$_5$ | (4) | C—CH$_3$ ‖ O |
| 69 | OHC—⟨phenyl⟩—O—(CH$_2$)$_2$—N⟨piperidine⟩ | H$_2$NNHCH$_2$CH$_2$OH | ⟨piperidine⟩N—(CH$_2$)$_2$ | (4) | CH$_2$CH$_2$OH |
| 70 | OHC—⟨phenyl⟩—O—(CH$_2$)$_3$—N⟨piperazine⟩N—C$_2$H$_5$ | H$_2$NNHCC$_2$H$_5$ ‖ O | C$_2$H$_5$—N⟨piperazine⟩N—(CH$_2$)$_3$ | (4) | C—C$_2$H$_5$ ‖ O |
| 71 | CHO—⟨phenyl⟩—O—(CH$_2$)$_2$—N—(CH$_3$)$_2$ | H$_2$NNHC$_2$H$_5$ | (CH$_3$)$_2$N(CH$_2$)$_2$ | (3) | C$_2$H$_5$ |
| 72 | CHO—⟨phenyl⟩—O—(CH$_2$)$_4$—NH(i-C$_3$H$_7$) | H$_2$NNHC$_2$H$_5$ | i-C$_3$H$_7$NH(CH$_2$)$_4$ | (2) | C$_2$H$_5$ |

-continued

| Ex. | I | II | III B-alkylene | (position) | IV R |
|---|---|---|---|---|---|
| 73 | CHO-C6H4-O-(CH2)3-N(piperidine) | H2NNHCH2C6H5 | piperidine-N-(CH2)3 | (3) | CH2C6H5 |
| 74 | CHO-C6H4-O-(CH2)3-N(hexamethyleneimine) | H2NNHCH2CH2C6H5 | hexamethyleneimine-N-(CH2)3 | (2) | CH2CH2C6H5 |
| 75 | CHO-C6H4-O-(CH2)3-N(morpholine) | H2NNHC2H5 | O(morpholine)N-(CH2)3 | (3) | C2H5 |
| 76 | CHO-C6H4-O-(CH2)3-N(piperazine)N-CH3 | H2NNHn-C3H7 | CH3-N(piperazine)N-(CH2)3 | (2) | n-C3H7 |
| 77 | CHO-C6H4-O-(CH2)3-N(piperazine)N-CH2CH2OH | H2NNHCH2C6H5 | HOCH2CH2-N(piperazine)N-(CH2)3 | (3) | CH2C6H5 |
| 78 | CHO-C6H4-O-(CH2)2-N-(CH3)2 | H2NNHC6H5 | (CH3)2N(CH2)2 | (3) | C6H5 |
| 79 | CHO-C6H4-O-(CH2)4-NH(C2H5) | H2NNHC(=O)CH3 | C2H5NH(CH2)4 | (3) | C(=O)CH3 |
| 80 | CHO-C6H4-O-(CH2)3-N(piperidine) | H2NNHCH2CH2OH | piperidine-N-(CH2)3 | (2) | CH2CH2OH |
| 81 | CHO-C6H4-O-(CH2)3-N(hexamethyleneimine) | H2NNHC6H5 | hexamethyleneimine-N-(CH2)3 | (2) | C6H5 |
| 82 | CHO-C6H4-O-(CH2)3-N(morpholine) | H2NNHC(=O)C2H5 | O(morpholine)N-(CH2)3 | (2) | C(=O)C2H5 |
| 83 | CHO-C6H4-(CH2)3-N(piperazine)N-C2H5 | H2NNHCH2CH2OH | C2H5-N(piperazine)N-(CH2)3 | (3) | CH2CH2OH |

EXAMPLES 84 to 104

Following the procedure of Example 6 but substituting for the benzaldehyde in part A an equivalent amount of the substituted benzaldehyde of column I, and substituting for methylhydrazine in part B an equivalent amount of the hydrazine listed in column II, there is obtained, respectively, the corresponding compound of the formula

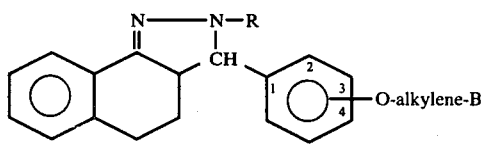

wherein B-alkylene is the radical indicated in column III and R is the radical indicated in column IV.

| Ex. | I | II | III B-alkylene | (position) | IV R |
|---|---|---|---|---|---|
| 84 | OHC—C₆H₄—O—(CH₂)₂—N(CH₃)₂ | H₂NNHC₂H₅ | (CH₃)₂N—(CH₂)₂ | (4) | C₂H₅ |
| 85 | OHC—C₆H₄—O—(CH₂)₄—NH(i-C₃H₇) | H₂NNHC₂H₅ | (i-C₃H₇)NH—(CH₂)₄ | (4) | C₂H₅ |
| 86 | OHC—C₆H₄—O—(CH₂)₃—N(piperidine) | H₂NNHCH₂C₆H₅ | piperidine-N—(CH₂)₃ | (4) | CH₂C₆H₅ |
| 87 | OHC—C₆H₄—O—(CH₂)₃—N(pyrrolidine) | H₂NNHCH₂CH₂C₆H₅ | pyrrolidine-N—(CH₂)₃ | (4) | CH₂CH₂C₆H₅ |
| 88 | OHC—C₆H₄—O—(CH₂)₃—N(morpholine) | H₂NNH₂ | O(morpholine)N—(CH₂)₃ | (4) | H |
| 89 | OHC—C₆H₄—O—(CH₂)₃—N(N'-methylpiperazine) | H₂NNHn-C₃H₇ | CH₃—N(piperazine)N—(CH₂)₃ | (4) | n-C₃H₇ |
| 90 | OHC—C₆H₄—O—(CH₂)₃—N(piperazine)N—CH₂CH₂OH | H₂NNHCH₂C₆H₅ | HOCH₂CH₂—N(piperazine)N—(CH₂)₃ | (4) | CH₂C₆H₅ |
| 91 | OHC—C₆H₄—O—(CH₂)₂—N(CH₃)₂ | H₂NNHC₆H₅ | (CH₃)₂—N(CH₂)₂ | (4) | C₆H₅ |
| 92 | OHC—C₆H₄—O—(CH₂)₄—NH(n-C₃H₇) | H₂NNHC(O)CH₃ | n-C₃H₇NH(CH₂)₄ | (4) | C(O)CH₃ |
| 93 | OHC—C₆H₄—O—(CH₂)₅—N(piperidine) | H₂NNHCH₂CH₂OH | piperidine-N—(CH₂)₅ | (4) | CH₂CH₂OH |
| 94 | 3-CHO-C₆H₄—O—(CH₂)₃—N(pyrrolidine) | H₂NNHCH₂CH₂C₆H₅ | pyrrolidine-N—(CH₂)₃ | (3) | CH₂CH₂C₆H₅ |
| 95 | 3-CHO-C₆H₄—O—(CH₂)₃—N(morpholine) | H₂NNHC₂H₅ | O(morpholine)N—(CH₂)₃ | (3) | C₂H₅ |
| 96 | 2-CHO-C₆H₄—O—(CH₂)₃—N(N'-methylpiperazine) | H₂NNHn-C₃H₇ | CH₃—N(piperazine)N—(CH₂)₂ | (2) | n-C₃H₇ |
| 97 | 2-CHO-C₆H₄—O—(CH₂)₃—N(piperazine)N—CH₂CH₂OH | H₂NNHCH₂C₆H₅ | HOCH₂CH₂—N(piperazine)N—(CH₂)₃ | (2) | CH₂C₆H₅ |
| 98 | 2-CHO-C₆H₄—O—(CH₂)₂—N(CH₃)₂ | H₂NNHC₂H₅ | (CH₃)₂N—(CH₂)₂ | (2) | C₂H₅ |

-continued

| Ex. | I | II | III B-alkylene | (position) | IV R |
|---|---|---|---|---|---|
| 99 | CHO, ⌬—O—(CH$_2$)$_4$—NH(n-C$_3$H$_7$) | H$_2$NNHC$_2$H$_5$ | n-C$_3$H$_7$NH(CH$_2$)$_4$ | (3) | C$_2$H$_5$ |
| 100 | CHO, ⌬—O—(CH$_2$)$_3$—N(C$_2$H$_5$)$_2$ | H$_2$NNHC$_6$H$_5$ | (C$_2$H$_5$)$_2$—N(CH$_2$)$_3$ | (2) | C$_6$H$_5$ |
| 101 | CHO, ⌬—O—(CH$_2$)$_3$—NHCH$_3$ | H$_2$NNHCH$_2$CH$_2$OH | (CH$_3$)HN(CH$_2$)$_3$ | (3) | CH$_2$CH$_2$OH |
| 102 | CHO, ⌬—O—(CH$_2$)$_3$—N(morpholino) | H$_2$NNHCOC$_2$H$_5$ | (morpholino)N—(CH$_2$)$_3$ | (3) | COC$_2$H$_5$ |
| 103 | CHO, ⌬—O—(CH$_2$)$_3$—N(piperazinyl-N'-CH$_3$) | H$_2$NNHC$_6$H$_5$ | CH$_3$—N(piperazinyl)N—(CH$_2$)$_3$ | (2) | C$_6$H$_5$ |
| 104 | CHO, ⌬—O—(CH$_2$)$_3$—N(piperazinyl-N'-CH$_2$CH$_2$OH) | H$_2$NNHCOCH$_3$ | HOCH$_2$CH$_2$—N(piperazinyl)N—(CH$_2$)$_3$ | (2) | COCH$_3$ |

EXAMPLES 105 to 126

Following the procedure of Example 2 but substituting for the benzaldehyde in part A an equivalent amount of the substituted benzaldehyde of column I, and substituting for indanone an equivalent amount of suberone, and substituting for methylhydrazine in part B an equivalent amount of the hydrazine list in column II, there is obtained, respectively, the corresponding compound of the formula

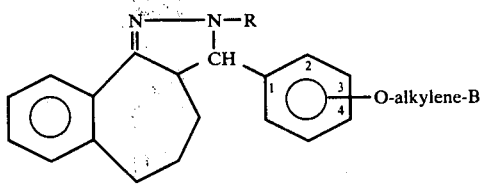

wherein B-alkylene is the radical indicated in column III and R is the radical indicated in column IV.

| Example | I | II | III B-alkylene | IV (position) | R |
|---|---|---|---|---|---|
| 105 | 4-OHC-C6H4-O-(CH2)2-N(CH3)2 | H2NNHC2H5 | (CH3)2N—(CH2)2 | (4) | C2H5 |
| 106 | 4-OHC-C6H4-O-(CH2)4-NH(C2H5) | H2NNHi-C3H7 | C2H5NH(CH2)4 | (4) | i-C3H7 |
| 107 | 4-OHC-C6H4-O-(CH2)3-N(piperidine) | H2NNHCH2C6H5 | piperidine-N—(CH2)3 | (4) | CH2C6H5 |
| 108 | 4-OHC-C6H4-O-(CH2)3-N(pyrrolidine) | H2NNHCH2CH2C6H5 | pyrrolidine-N—(CH2)3 | (4) | CH2CH2C6H5 |
| 109 | 4-OHC-C6H4-O-(CH2)3-N(morpholine) | H2NNHC2H5 | morpholine-N—(CH2)3 | (4) | C2H5 |
| 110 | 4-OHC-C6H4-O-(CH2)3-N(4-methylpiperazine) | H2NNHn-C3H7 | CH3-N(piperazine)N—(CH2)3 | (4) | n-C3H7 |
| 111 | 4-OHC-C6H4-O-(CH2)3-N(4-(2-hydroxyethyl)piperazine) | H2NNHCH2C6H5 | HOCH2CH2-N(piperazine)N—(CH2)3 | (4) | CH2C6H5 |
| 112 | 2-CHO-C6H4-O-(CH2)2-N(CH3)2 | H2NNH2 | (CH3)2N—(CH2)2 | (2) | H |
| 113 | 2-CHO-C6H4-O-(CH2)4-NH(i-C3H7) | H2NNHi-C3H7 | (i-C3H7)NH(CH2)4 | (2) | i-C3H7 |

-continued

| Example | I | II | III B-alkylene | IV (position) | R |
|---|---|---|---|---|---|
| 114 | CHO-[3-(piperidin-1-yl)propoxy]phenyl | H₂NNHCH₂C₆H₅ | piperidine-N-(CH₂)₃ | (3) | CH₂C₆H₅ |
| 115 | CHO-[3-(pyrrolidin-1-yl)propoxy]phenyl | H₂NNHCH₂CH₂C₆H₅ | pyrrolidine-N-(CH₂)₃ | (3) | CH₂CH₂C₆H₅ |
| 116 | CHO-[3-(morpholin-4-yl)propoxy]phenyl | H₂NNHC₂H₅ | morpholine-N-(CH₂)₃ | (2) | C₂H₅ |
| 117 | CHO-[3-(4-methylpiperazin-1-yl)propoxy]phenyl | H₂NNHn-C₃H₇ | CH₃—N(piperazine)—(CH₂)₃ | (2) | n-C₃H₇ |
| 118 | CHO-[3-(4-(2-hydroxyethyl)piperazin-1-yl)propoxy]phenyl | H₂NNHCH₂C₆H₅ | HOCH₂CH₂—N(piperazine)—(CH₂)₃ | (2) | CH₂C₆H₅ |
| 119 | OHC-[4-(2-diethylaminoethoxy)]phenyl | H₂NNHCC₂H₅ (C=O) | (C₂H₅)₂N—(CH₂)₂ | (4) | CC₂H₅ (C=O) |
| 120 | CHO-[3-(2-dimethylaminoethoxy)]phenyl | H₂NNHC₆H₅ | (CH₃)₂N(CH₂)₂ | (4) | C₆H₅ |
| 121 | CHO-[2-(4-ethylaminobutoxy)]phenyl | H₂NNHCH₂CH₂OH | C₂H₅NH(CH₂)₄ | (2) | CH₂CH₂OH |

-continued

| Example | I | II | III B-alkylene | IV (position) | R |
|---------|---|----|----|----|----|
| 122 | 4-[piperidino-(CH$_2$)$_3$-O]-benzaldehyde (OHC-C$_6$H$_4$-O-(CH$_2$)$_3$-N-piperidine) | H$_2$NNHC$_6$H$_5$ | N-(CH$_2$)$_3$ piperidine | (4) | C$_6$H$_5$ |
| 123 | 3-[pyrrolidino-(CH$_2$)$_3$-O]-benzaldehyde with CHO | H$_2$NNHCH$_2$CH$_2$OH | N-(CH$_2$)$_3$ pyrrolidine | (3) | CH$_2$CH$_2$OH |
| 124 | 2-[morpholino-(CH$_2$)$_3$-O]-benzaldehyde with CHO | H$_2$NNHCC$_2$H$_5$ (O=) | N-(CH$_2$)$_3$ morpholine | (2) | CC$_2$H$_5$ (O=) |
| 125 | 3-[(4-methylpiperazino)-(CH$_2$)$_3$-O]-benzaldehyde with CHO | H$_2$NNHC$_6$H$_5$ | CH$_3$-N piperazine N-(CH$_2$)$_3$ | (3) | C$_6$H$_5$ |
| 126 | 3-[(4-hydroxyethylpiperazino)-(CH$_2$)$_3$-O]-benzaldehyde | H$_2$NNHC$_6$H$_5$ | HOCH$_2$CH$_2$-N piperazine N-(CH$_2$)$_3$ | (3) | C$_6$H$_5$ |

EXAMPLES 127 – 147

Following the procedure of Example 1 but substituting for 1-indanone in part A the substituted 2-benzal-1-indanone of the formula

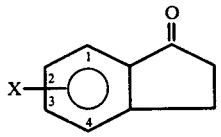

wherein X is the substituent in the positions indicated below in column I, substituting for the benzaldehyde in part A an equivalent amount of the substituted benzaldehyde of column II, and substituting for methylhydrazine in part B an equivalent amount of the hydrazine listed in column IV, there is obtained, respectively, the corresponding compound of the formula

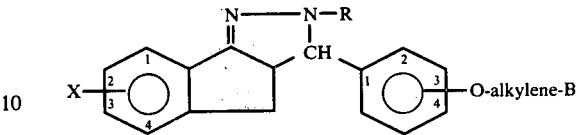

wherein B-alkylene is as indicated in column IV and R is as indicated in column V and X is as indicated in column I.

| Ex | I X 1 | 2 | 3 | 4 | II | III | IV B-alkylene | V (position) | R |
|---|---|---|---|---|---|---|---|---|---|
| 127 | Cl | | | | OHC-C6H4-O-(CH2)2-N(CH3)2 | H2NNHC2H5 | (CH3)2N(CH2)2 | (4) | C2H5 |
| 128 | Cl | | | | OHC-C6H4-O-(CH2)4-NHC2H5 | H2NNHn-C3H7 | C2H5NH(CH2)4 | (4) | n-C3H7 |
| 129 | | | F | | OHC-C6H4-O-(CH2)3-N(piperidine) | H2NNHCH2C6H5 | N(CH2)5 (piperidine) | (4) | CH2C6H5 |
| 130 | CH3 | | | | OHC-C6H4-O-(CH2)3-N(pyrrolidine) | H2NNHCH2CH2C6H5 | N(CH2)4 (pyrrolidine) | (4) | CH2CH2C6H5 |
| 131 | | | | C2H5 | OHC-C6H4-O-(CH2)3-N(morpholine) | H2NNH2 | morpholine-(CH2)3 | (4) | H |
| 132 | CF3 | | | | OHC-C6H4-O-(CH2)3-N(N-CH3 piperazine) | H2NNHi-C3H7 | CH3-N(piperazine)-(CH2)3 | (4) | i-C3H7 |
| 133 | | | OCH3 | | OHC-C6H4-O-(CH2)3-N(N-CH2CH2OH piperazine) | H2NNHC6H5 | HOCH2CH2-N(piperazine)-(CH2)3 | (4) | CH2C6H5 |
| 134 | Cl | | | | OHC-C6H4-O-(CH2)5-N(CH3)2 | H2NNHC(O)n-C3H7 | (CH3)2N(CH2)5 | (4) | C6H5 |
| 135 | Cl | | | | OHC-C6H4-O-(CH2)4-NH(C2H5) | H2NNHCH2CH2CH2OH | C2H5NH(CH2)4 | (4) | O=Cn-C3H7 |
| 136 | | | F | | OHC-C6H4-O-(CH2)3-N(piperidine) | H2NNHCH2CH2CH2OH | N(CH2)5 (piperidine) | (4) | CH2CH2CH2OH |

-continued

| Ex | I X 1 | 2 | 3 | 4 | II | III | IV B-alkylene | V (position) | R |
|---|---|---|---|---|---|---|---|---|---|
| 137 | CH₃ | | | | 2-CHO-phenyl-O-(CH₂)₃-N(pyrrolidine) | H₂NNHCH₂C₆H₅ | pyrrolidine-N-(CH₂)₃ | (2) | CH₂CH₂C₆H₅ |
| 138 | | C₂H₅ | | | 2-CHO-phenyl-O-(CH₂)₃-N(morpholine) | H₂NNHC₂H₅ | morpholine-N-(CH₂)₃ | (2) | C₂H₅ |
| 139 | CF₃ | | OCH₃ | | 3-CHO-phenyl-O-(CH₂)₃-N(4-CH₃-piperazine) | H₂NNHn-C₃H₇ | 4-CH₃-piperazine-N-(CH₂)₃ | (3) | n-C₃H₇ |
| 140 | | | | | 3-CHO-phenyl-O-(CH₂)₃-N(4-CH₂CH₂OH-piperazine) | H₂NNHCH₂C₆H₅ | 4-HOCH₂CH₂-piperazine-N-(CH₂)₃ | (3) | CH₂C₆H₅ |
| 141 | Cl | | | | 3-CHO-phenyl-O-(CH₂)₂-N(CH₃)₂ | H₂NNHC₆H₅ | (CH₃)₂N(CH₂)₂ | (3) | C₆H₅ |
| 142 | Cl | | | | 2-CHO-phenyl-O-(CH₂)₄-NH(i-C₃H₇) | H₂NNHC(O)C₂H₅ | i-C₃H₇NH(CH₂)₄ | (2) | C(O)C₂H₅ |
| 143 | F | | | | 3-CHO-phenyl-O-(CH₂)₃-N(piperidine) | H₂NNHCH₂CH₂OH | piperidine-N-(CH₂)₃ | (3) | CH₂CH₂OH |
| 144 | CH₃ | | | | 3-CHO-phenyl-O-(CH₂)₃-N(pyrrolidine) | H₂NNHC₆H₅ | pyrrolidine-N-(CH₂)₃ | (3) | C₆H₅ |

-continued

| Ex | X1 | X2 | X3 | X4 | II | III | IV B-alkylene | V (position) | R |
|---|---|---|---|---|---|---|---|---|---|
| 145 | | | | C₂H₅ | CHO, phenyl with O-(CH₂)₃-morpholine | H₂NNHC(O)CH₃ | morpholine-N-(CH₂)₃- | (2) | -C(=O)CH₃ |
| 146 | CF₃ | | | | CHO, phenyl with O-(CH₂)₃-(4-ethylpiperazin-1-yl) | H₂NNHC₆H₅ | (4-ethylpiperazin-1-yl)-(CH₂)₃- | (2) | C₆H₅ |
| 147 | | | OCH₃ | | CHO, phenyl with O-(CH₂)₃-(4-(2-hydroxyethyl)piperazin-1-yl) | H₂NNHC₆H₅ | HOCH₂CH₂-(4-piperazinyl)-N-(CH₂)₃- | (3) | C₆H₅ |

EXAMPLES 148 – 168

Following the procedure of Example 6 but substituting the substituted 1-tetralone of the formula

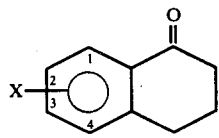

wherein X is the substituent in the positions indicated below in column I, substituting for the benzaldehyde in part A an equivalent amount of the substituted benzaldehyde of column II, and substituting for methylhydrazine in part B an equivalent amount of the hydrazine listed in column III, there is obtained, respectively, the corresponding compound of the formula

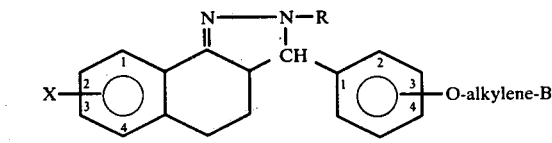

wherein B-alkylene is as indicated in column IV and R is as indicated in column V and X is as indicated in column I.

| Ex. | I X 1 | 2 | 3 | 4 | II | III | IV B-alkylene | (position) | V R |
|---|---|---|---|---|---|---|---|---|---|
| 148 | Cl | | | | OHC-C6H4-O-(CH2)2-N(CH3)2 | H2NNHC2H5 | (CH3)2N(CH2)2 | (4) | C2H5 |
| 149 | | Cl | | | OHC-C6H4-O-(CH2)4-NHC2H5 | H2NNHn-C3H7 | C2H5NH(CH2)4 | (4) | n-C3H7 |
| 150 | | | F | | OHC-C6H4-O-(CH2)3-N(piperidine) | H2NNHCH2C6H5 | N(piperidine)-(CH2)3 | (4) | CH2C6H5 |
| 151 | CH3 | | | | OHC-C6H4-O-(CH2)3-N(pyrrolidine) | H2NNHCH2CH2C6H5 | N(pyrrolidine)-(CH2)3 | (4) | CH2CH2C6H5 |
| 152 | | | | C2H5 | OHC-C6H4-O-(CH2)3-N(morpholine) | H2NNHC2H5 | N(morpholine)-(CH2)3 | (4) | C2H5 |
| 153 | CF3 | | | | OHC-C6H4-O-(CH2)3-N(N-CH3 piperazine) | H2NNHi-C3H7 | CH3-N(piperazine)-N-(CH2)5 | (4) | i-C3H7 |
| 154 | | | OCH3 | | OHC-C6H4-O-(CH2)3-N(N-CH2CH2OH piperazine) | H2NNHCH2C6H5 | HOCH2CH2-N(piperazine)-N-(CH2)3 | (4) | CH2C6H5 |
| 155 | | Cl | | | OHC-C6H4-O-(CH2)2-N(CH3)2 | H2NNHC6H5 | (CH3)2N(CH2)3 | (4) | C6H5 |
| 156 | | Cl | | | OHC-C6H4-O-(CH2)4-NH(C2H5) | H2NNHC(O)C3H7 | C2H5NH(CH2)4 | (4) | O=C-n-C3H7 |
| 157 | | | F | | OHC-C6H4-O-(CH2)3-N(piperidine) | H2NNHCH2CH2CH2OH | N(piperidine)-(CH2)3 | (4) | CH2CH2CH2OH |

-continued

| Ex. | I X 1 2 3 4 | II | III | IV B-alkylene | V R (position) |
|---|---|---|---|---|---|
| 158 | CH₃ | CHO, O—(CH₂)₃—N(pyrrolidine) | H₂NNHCH₂CH₂C₆H₅ | N—(CH₂)₃ (pyrrolidine) | CH₂CH₂C₆H₅ (2) |
| 159 | C₂H₅ | CHO, O—(CH₂)₃—N(morpholine) | H₂NNHC₂H₅ | N—(CH₂)₃ (morpholine, O) | C₂H₅ (2) |
| 160 | CF₃ | OCH₃ | CHO, O—(CH₂)₃—N(N-CH₃ piperazine) | H₂NNHn-C₃H₇ | CH₃—N—(CH₂)₃ (piperazine) | n-C₃H₇ (3) |
| 161 | Cl | | CHO, O—(CH₂)₃—N(N-CH₂CH₂OH piperazine) | H₂NNHCH₂C₆H₅ | HOCH₂CH₂—N—(CH₂)₃ (piperazine) | CH₂C₆H₅ (3) |
| 162 | Cl | | CHO, O—(CH₂)₂—N(CH₃)₂ | H₂NNHC₆H₅ | (CH₃)₂N(CH₂)₂ | C₆H₅ (3) |
| 163 | F | | CHO, O—(CH₂)₄—NH(i-C₃H₇) | H₂NNHCC₂H₅ (O=) | i-C₃H₇NH(CH₂)₄ | O=CC₂H₅ (2) |
| 164 | | | CHO, O—(CH₂)₃—N(piperidine) | H₂NNHCH₂CH₂OH | N—(CH₂)₃ (piperidine) | CH₂CH₂OH (3) |
| 165 | CH₃ | | O—(CH₂)₃—N(pyrrolidine) | H₂NNHC₆H₅ | N—(CH₂)₃ (pyrrolidine) | C₆H₅ (3) |

-continued

| Ex. | 1 | X 2 | 3 | 4 | II | III | IV B-alkylene | (position) | V R |
|---|---|---|---|---|---|---|---|---|---|
| 166 | | | | C₂H₅ | ![structure: 2-CHO phenyl with O-(CH₂)₃-morpholine] | H₂NNHC(O)CH₃ | morpholine-N-(CH₂)₃- | (2) | O=CCH₃ |
| 167 | CF₃ | | | | ![structure: 2-CHO phenyl with O-(CH₂)₃-N-piperazine-N-C₂H₅] | H₂NNHC₆H₅ | C₂H₅-N-piperazine-N-(CH₂)₃- | (2) | C₆H₅ |
| 168 | | | OCH₃ | | ![structure: 3-CHO phenyl with O-(CH₂)₃-N-piperazine-N-CH₂CH₂OH] | H₂NNHC₆H₅ | HOCH₂CH₂-N-piperazine-N-(CH₂)₃- | (3) | C₆H₅ |

EXAMPLES 169 – 189

Following the procedure of Example 1 but substituting for the indanone in part A the substituted suberone of the formula

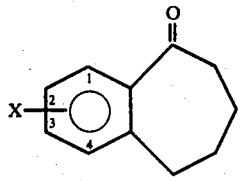

wherein X is the substituent in the positions indicated below in column I, substituting for the benzaldehyde in part A an equivalent amount of the substituted benzaldehyde of column II, and substituting for methylhydrazine in part B an equivalent amount of the hydrazine listed in column IV, there is obtained, respectively, the corresponding compound of the formula

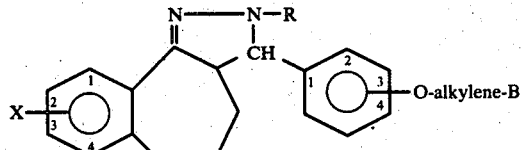

wherein B-alkylene is as indicated in column IV and R is as indicated in column V and X is as indicated in column I.

| Ex. | X 1 | 2 | 3 | 4 | II | III | IV B-alkylene | V (position) | R |
|---|---|---|---|---|---|---|---|---|---|
| 169 | Cl | | | | OHC-⟨C6H4⟩-O-(CH2)2-N(CH3)2 | H2NNHC2H5 | (CH3)2N(CH2)2 | (4) | C2H5 |
| 170 | | Cl | | | OHC-⟨C6H4⟩-O-(CH2)4-NHC2H5 | H2NNHn-C3H7 | C2H5NH(CH2)4 | (4) | n-C3H7 |
| 171 | | | F | | OHC-⟨C6H4⟩-O-(CH2)3-N(piperidine) | H2NNHCH2C6H5 | N-(CH2)5 (piperidine) | (4) | CH2C6H5 |
| 172 | CH3 | | | | OHC-⟨C6H4⟩-O-(CH2)3-N(pyrrolidine) | H2NNHCH2CH2C6H5 | N-(CH2)3 (pyrrolidine) | (4) | CH2CH2C6H5 |
| 173 | | | C2H5 | | OHC-⟨C6H4⟩-O-(CH2)3-N(morpholine) | H2NNHC2H5 | O-morpholine-N-(CH2)3 | (4) | C2H5 |
| 174 | CF3 | | | | OHC-⟨C6H4⟩-O-(CH2)3-N(N-CH3 piperazine) | H2NNHi-C3H7 | CH3-N-piperazine-N-(CH2)3 | (4) | i-C3H7 |
| 175 | | | OCH3 | | OHC-⟨C6H4⟩-O-(CH2)3-N(N-CH2CH2OH piperazine) | H2NNHCH2C6H5 | HOCH2CH2-N-piperazine-N-(CH2)3 | (4) | CH2C6H5 |
| 176 | Cl | | | | OHC-⟨C6H4⟩-O-(CH2)2-N(CH3)2 | H2NNHC6H5 | (CH3)2N(CH2)2 | (4) | C6H5 |
| 177 | | Cl | | | OHC-⟨C6H4⟩-O-(CH2)4-NH(C2H5) | H2NNHCCH3 (O=) | C2H5NH(CH2)4 | (4) | O=Cn-C3H7 |
| 178 | | | F | | OHC-⟨C6H4⟩-O-(CH2)3-N(piperidine) | H2NNHCH2CH2OH | N-(CH2)5 (piperidine) | (4) | CH2CH2OH |

4,053,514

-continued

| Ex. | I X 1 2 3 4 | II | III | IV B-alkylene | V (position) | R |
|---|---|---|---|---|---|---|
| 179 | CH₃ | 2-CHO-phenyl-O-(CH₂)₃-N(pyrrolidine) | H₂NNHCH₂CH₂C₆H₅ | pyrrolidine-N-(CH₂)₃ | (2) | CH₂CH₂C₆H₅ |
| 180 | C₂H₅ | 2-CHO-phenyl-O-(CH₂)₃-N(morpholine) | H₂NNHC₂H₅ | morpholine-N-(CH₂)₃ | (2) | C₂H₅ |
| 181 | CF₃, OCH₃ | 3-CHO-phenyl-O-(CH₂)₃-N(N-CH₃-piperazine) | H₂NNHn-C₃H₇ | CH₃-piperazine-N-(CH₂)₃ | (3) | n-C₃H₇ |
| 182 | Cl | 3-CHO-phenyl-O-(CH₂)₃-N(N-CH₂CH₂OH-piperazine) | H₂NNHCH₂C₆H₅ | HOCH₂CH₂-piperazine-N-(CH₂)₃ | (3) | CH₂C₆H₅ |
| 183 | Cl | 3-CHO-phenyl-O-(CH₂)₂-N-N(CH₃)₂ | H₂NNHC₆H₅ | (CH₃)₂N(CH₂)₂ | (3) | C₆H₅ |
| 184 | F | 2-CHO-phenyl-O-(CH₂)₄-NH(i-C₃H₇) | H₂NNHCOC₂H₅ | i-C₃H₇NH(CH₂)₄ | (2) | O=CC₂H₅ |
| 185 | | 3-CHO-phenyl-O-(CH₂)₃-N(piperidine) | H₂NNHCH₂CH₂OH | piperidine-N-(CH₂)₃ | (3) | CH₂CH₂OH |
| 186 | CH₃ | 3-CHO-phenyl-O-(CH₂)₃-N(pyrrolidine) | H₂NNHC₆H₅ | pyrrolidine-N-(CH₂)₃ | (3) | C₆H₅ |

-continued

| Ex. | I X 1 2 3 4 | II | III | IV B-alkylene | (position) | V R |
|---|---|---|---|---|---|---|
| 187 | C₂H₅ | ![structure: phenyl with CHO and O-(CH₂)₃-morpholine] | H₂NNHCCH₃ (with =O) | N(morpholine)—(CH₂)₃ | (2) | O=CCH₃ |
| 188 | CF₃ | ![structure: phenyl with CHO and O-(CH₂)₃-N-piperazine-N-C₂H₅] | H₂NNHC₆H₅ | C₂H₅—N(piperazine)—N—(CH₂)₃ | (2) | C₆H₅ |
| 189 | OCH₃ | ![structure: phenyl with CHO and O-(CH₂)₃-N-piperazine-N-CH₂CH₂OH] | H₂NNHC₆H₅ | HOCH₂CH₂—N(piperazine)—N—(CH₂)₃ | (3) | C₆H₅ |

EXAMPLE 190

3-[4-[2-(Dimethylamino)ethoxy]phenyl]-2,3,3a,4-tetrahydro-2-methylindeno[1,2-c]pyrazolo, N-oxide A solution of the free base from Example 1B in acetonitrile is treated with two equivalents of hydrogen peroxide in acetic acid and the solution allowed to stand at room temperature for 8 hours. The solvent is removed to give the product.

What is claimed is:

1. A compound of the formula

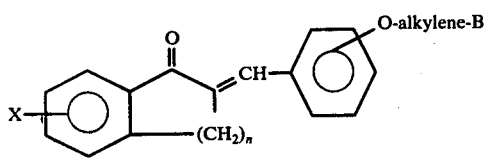

wherein X is a member selected from the group consisting of H, halogen, alkyl of from 1 to 8 carbons, lower alkoxy or $CF_3$; $n$ is 1, 2 or 3; B is a member selected from the group consisting of lower alkylamino, and dilower alkylamino; and alkylene is a straight or branched saturated hydrocarbon chain group containing from 2 to about 5 carbons; and N-oxides and pharmaceutically acceptable acid-addition salts thereof.

2. A compound according to claim 1 wherein $n$ is 1.

3. A compound according to claim 1 wherein $n$ is 2.

4. A compound according to claim 1 wherein B is lower alkyl amino wherein the alkyl group has from 1 to 4 carbons, or dilower alkylamino wherein each alkyl group has from 1 to 4 carbons.

5. A compound as defined in claim 1 wherein $n$ is 1 or 2, X is H, O-alkylene-B is in the meta or para positions, alkylene contains 2 or 3 carbons, and B is dialkylamino.

6. A compound according to claim 1 having the name 2-[[b4-[(diethylamino)ethoxy]phenyl]methylene]2,3-dihydro-1H-indene-1-one or its hydrochloride salt.

7. A compound according to claim 1 having the name 2-[[4-[3-(dimethylamino)propoxy]phenyl]methylene]-2,3-dihydro-1H-indene-1-one or its hydrochloride salt.

8. A compound according to claim 1 having the name 2-[[3-[3-(dimethylamino)propoxy]phenyl]methylene]-2,3-dihydro-1H-inden-1-one or its hydrochloride salt.

9. A compound according to claim 1 having the name 2-[[2-[3-(dimethylamino)propoxy]phenyl]methylene]-2,3-dihydro-1H-inden-1-one or its hydrochloride salt.

10. A compound according to claim 1 having the name 2-[[4-[2-(diethylamino)ethoxy]phenyl]methylene]-3,4-dihydro-1(2H)-naphthalenone or its hydrochloride salt.

11. A compound according to claim 1 having the name 2-[[4-[2-(dimethylamino)ethoxy]phenyl]methylene]-2,3-dihydro-1H-inden-1-one or its hydrochloride salt.

* * * * *

UNITED STATES PATENT OFFICE
CERTIFICATE OF CORRECTION

Patent No. 4,053,514  Dated October 11, 1977

Inventor(s) John Krapcho et al.

It is certified that error appears in the above-identified patent and that said Letters Patent are hereby corrected as shown below:

Column 3, line 24, "[" should read --]--.
Column 3, line 59, "of" should read --or--.
Column 5, line 56, "148°" should read --147°--.
Column 7, line 3, "[1,2-d]" should read --[1,2-c]--.
Column 8, line 13, "1.0" should read --10.0--.
Column 8, line 36, before the title insert --B.--.
Columns 17 and 18, Example 83, Column I, the formula should read

--  --.

Columns 19 and 20, Example 91, Column III, the formula should read --$(CH_3)_2$-$N(CH_2)_2$--.
Columns 21 and 22, Example 100, Columns II and III, the formulae should read --$H_2NNHC_6H_5$-- and --$(C_2H_5)_2$-$N(CH_2)_3$-- respectively.--
Column 21, line 34, "Example 2" should read --Example 1--.
Column 21, line 39, "list" should read --listed--.
Column 54, line 10, "2-[[b4-" should read --2-[[4- --.

Signed and Sealed this

Fourteenth Day of February 1978

[SEAL]

Attest:

RUTH C. MASON  
*Attesting Officer*

LUTRELLE F. PARKER  
*Acting Commissioner of Patents and Trademarks*